(12) United States Patent
Baum et al.

(10) Patent No.: US 7,070,992 B2
(45) Date of Patent: Jul. 4, 2006

(54) RETROVIRAL VECTORS WITH FOREIGN-SEQUENCE INSERTION BETWEEN RETROVIRAL PRIMER BINDING SITE AND RETROVIRAL SPLICE DONOR

(75) Inventors: Christopher Baum, Hamburg (DE); Daniel Schaumann, Reinbek (DE)

(73) Assignee: Heinrich-Pette-Institute, Hamburg (DE)

( * ) Notice: Subject to any disclaimer, the term of this patent is extended or adjusted under 35 U.S.C. 154(b) by 0 days.

(21) Appl. No.: 09/953,572

(22) Filed: Sep. 10, 2001

(65) Prior Publication Data

US 2002/0160971 A1    Oct. 31, 2002

(30) Foreign Application Priority Data

Sep. 12, 2000   (DE)  ................................ 100 45 016

(51) Int. Cl.
*C12N 1/00*      (2006.01)
*C12N 15/09*   (2006.01)
*C12N 15/63*   (2006.01)
*C12N 15/70*   (2006.01)
*C12N 15/74*   (2006.01)

(52) U.S. Cl. ................... 435/325; 435/455; 435/320.1; 435/69.1; 435/91.4; 514/44; 424/93.1

(58) Field of Classification Search .............. 435/320.1, 435/455, 325, 69.1, 91.4
See application file for complete search history.

(56) References Cited

FOREIGN PATENT DOCUMENTS

DE          19822115 A1       11/1999

OTHER PUBLICATIONS

Hirota et al.,, Leukemia, 11 Suppl 3, 102-5, Apr. 1997.*
Lodmell (Antisense and Nucleic Acid Drug Development, 8, 6, 517-29, 1998).*
Guesdon et al. Virology. 2001, vol. 288, pp. 81-88.*
Hildinger et al., "Design of 5' Untranslated Sequences in Retroviral Vectors Developed for Medical Use," *J. Virol.*, 73(5) :4083-4089 (1999).

* cited by examiner

*Primary Examiner*—Joseph Woitach
*Assistant Examiner*—Robert M. Kelly
(74) *Attorney, Agent, or Firm*—McDermott Will & Emery LLP

(57) ABSTRACT

The subject of the invention is retroviral gene transfer vectors in which foreign sequences are introduced between the retroviral primer binding site (PBS) and the retroviral splice donor (SD). The efficiency of gene expression is improved by this modification, and the vectors are characterized by an increased reliability during use.

54 Claims, 7 Drawing Sheets

RETROVIRAL VECTORS WITH FOREIGN-SEQUENCE INSERTION BETWEEN RETROVIRAL PRIMER BINDING SITE AND RETROVIRAL SPLICE DONOR

This application claims priority under 35 U.S.C. § 119 to German patent application 100 45 016.4, filed Sep. 12, 2000. A biological deposit under the Budapest Treaty was received at the Deutsche Sammlung von Mikroorganismen und Zellkulturen GmbH (DSMZ) on Aug. 31, 2000. The deposit was identified as pSMICIP2s(eGFP) and given accession number DSM 13711.

The subject of the invention is retroviral gene transfer vectors in which foreign sequences are introduced between the retroviral primer binding site (PBS) and the retroviral splice donor (SD). The efficiency of gene expression is improved by this modification, and the vectors are characterized by an increased reliability during use.

Conventional retroviral vectors have the structure shown schematically in FIG. 1, foreign sequences being incorporated either downstream of the splice acceptor signal (SA), downstream of the splice donor signal (SD) or inside the terminal sequence repeats (long terminal repeat, LTR) of the retroviral vector.

There is a demand for vectors which are characterized by an improved gene expression and high level of biological safety.

This object is achieved according to the invention by the retroviral vectors of patent claims 1 to 8.

Within the framework of the present invention it was surprisingly established that retroviral vectors with the general structure

5'-[LTR]-[PBS]-[SD]-[ψ]-[SA]-[PP]-[LTR]-3', in which
 [LTR] is the terminal sequence repeat (long terminal repeat, LTR) of the retroviral vector,
 [PBS] is the retroviral primer binding site,
 [SD] is the retroviral splice donor signal,
 [ψ] is the retroviral packaging signal,
 [SA] is the retroviral splice acceptor signal, and
 [PP] is a polypurine tract (PP tract), display substantial advantages vis-à-vis the state of the art, if a foreign sequence [FS1] which is selected from the group composed of enhancer-promoter sequences (e.g. from mouse-spleen-focus-forming virus), enhancer sequences (also without promoter), cDNA sequences (which code for a protein to be expressed) sequences for chromatin-modification such as matrix-attachment regions (MAR, e.g. of the human interferon-β gene), and/or sequences for RNA processing signals (e.g. post-transcriptional regulator element of the Woodchuck hepatitis virus) is inserted between the retroviral primer binding site (PDS) and the retroviral splice donor (SD).

Each DNA sequence which was not introduced in the natural, evolutionary way, but via targeted molecular-genetic methods, is to be regarded as a foreign sequence within the meaning of the invention.

If the enhancer/promoter is at the same time removed from the U3 region of the LTR (Yu et al., 1986), a thus-modified vector is characterized by increased biological safety, as the vector sequence cannot be mobilized upon infection with replication-competent retroviruses. The risk of activating downstream cellular sequences is reduced. Compared with conventional constructs, the vector according to the invention is characterized by an at least equivalent efficiency of gene expression.

The described modification vis-à-vis vectors in the state of the art is that the vectors according to the invention contain a foreign sequence [FS1] which is introduced upstream of the retroviral splice donor signal (SD)—which is still located in front of the packaging signal (cf. FIGS. 1 and 2) and downstream of the retroviral primer binding site (PBS). A second foreign sequence (foreign sequence 2, FS2) can be introduced downstream of the splice donor or packaging signal, as in conventional retroviral vectors (Hildinger et al.,1999; Deffaud und Darlix, 2000). [FS2] is preferably inserted between [SA] and [PP], the presence of the [SA] not being a necessary prerequisite for the vectors according to the invention. The terminal sequence repeat (long terminal repeat, LTR) of the retroviral vector can also contain such foreign sequences (FS3). According to the invention, the vector can contain, as foreign sequence according to the above definition, either only [FS1] or else [FS1] in combination with [FS2] and/or [FS3].

The foreign sequence [FS2] is preferably selected from the group consisting of cDNA sequences (e.g. coding for enhanced green fluorescent protein), enhancer and/or promoter sequences, sequences for internal ribosomal entry sites (IRES), sequences for matrix-attachment regions (MAR, e.g. of the human interferon-β-gene) and/or sequences for RNA processing signals (e.g. post-transcriptional regulator element of the Woodchuck hepatitis virus).

The foreign sequence [FS3] is preferably selected from the group consisting of cloning sites for the deletion of the LTR-enhancer promoter, enhancer and/or promoter sequences, cDNA sequences, sequences for matrix-attachment regions (MAR, e.g. of the human interferon-β gene) and/or sequences for RNA-processing signals (e.g. post-transcriptional regulator element of the Woodchuck hepatitis virus)

According to a preferred version of the invention, the vector contains the following foreign sequences:
 [FS1]: Fragment from the LTR of the mouse-spleen-focus-forming retrovirus (SFFVp) which contains the retroviral enhancer-promoter and the first 27 base pairs of the 5'-untranslated region of the retrovirus (Baum et al., 1995).
 [FS2]: Coding sequences (cDNA) of the enhanced green fluorescent protein (EGFP; Yang et al., 1996) with 3' following, non-coding gene fragment of the human interferon-β gene which contains a matrix-attachment region (MAR) (Schübeler et al., 1996).
 [FS3]: Artificial cloning site for the deletion of the LTR enhancer-promoter (cf. Yu et al., 1986).

This vector, called SMICIP2s(eGFP), contains 5' of the packaging signal, the retroviral splice donor and 3' of the packaging signal, a splice acceptor sequence (SA). Two preferred variants and two control vectors exist for this vector (SMICIP2s(eGFP)):
 Variant 1: as SMICIP2s(eGFP), but the MAR-sequences are missing (vector SINoM-EGFP);
 Variant 2: as variant 1, however the splice donor or splice acceptor sequences are also missing (vector SINoMS-EGFP);
 Control vector 1: the enhancer-promoter in the foreign sequence 1 was deleted and introduced into the foreign sequence 2 in front of the EGFP-cDNA instead (vector SINoMI-EGFP)—represents conventional vectors with self-inactivating LTR (Yu et al., 1986);

Control vector 2: Represents the conventional vector type with intact LTR (FIG. 1B) without foreign sequence 1 (vector SF110-EGFP; Hildinger et al., 1999).

These vectors were cloned as proviral plasmids based on pUC19 in *E. coli*. The plasmids contain the enhancer-promoter (U3 region) of the MPSV retrovirus in the 5' LTR. This sequence lies upstream of the cap position and is therefore not to be found again after transfection into eukaryotic packaging cells in the retroviral transcript. The retroviral transgene is constituted in retrovirally transduced target cells according to the structure shown in FIG. 1, the LTR sequences deriving from the 3' LTR of the plasmid with regard to the U3 region of the vector, the R and U5 sequences on the other hand from the 5' LTR of the plasmid. The proviral plasmid of the vector SMICIP2s (eGFP) is called pSMICIP2s (eGFP); the sequence of this plasmid is reproduced below in the sequence protocol. A specimen of this plasmid was deposited on Aug. 31, 2000 at the Deutsche Sammlung von Mikroorganismen und Zellkulturen (DSMZ), Mascheroder Weg 1b, 38124 Brunswick under the no. DSM 13711.

The vector SMICIP2s (eGFP) is characterized in that
1) a strong retroviral enhancer/promoter of the SFFVp retrovirus (Baum et al., 1995) was inserted between PBS and SD (=FS1),
2) the EGFP cDNA with following MAR sequence of the human interferon-beta gene (Schubeler et al., 1996) was used as [FS2] downstream of the [SA] and upstream of the [PP], and
3) a restriction site which replaces the enhancer/promoter of the U3 region of the LTR is present as [FS3].

In this combination by way of example, infectious titres and expression properties can be achieved in the transduced target cells which are at least comparable with conventional vectors without [FS1]. The reliability-relevant features of the novel vector are superior to the conventional constructs. For the first time, it has been shown in the sequence combination present in the vector SMICIP2s (eGFP) that a retroviral vector can contain an enhancer/promoter lying internally between the LTR sequences, with downstream intron in the 5' untranslated region, the insertion of the foreign sequences taking place in the sense orientation of the retroviral RNA.

According to a particular version, the invention furthermore relates to a vector in which the retroviral splice donor signal (SD) and/or the retroviral splice acceptor signal (SA) is/are inactivated by mutation.

The retrovirus used for the vector construction according to the invention is selected from the group composed of mouse-leukemia viruses, bird retroviruses (including spleen necrosis virus), spumaviruses (including human foamy virus), B-type retroviruses (including mouse-mammary tumor virus), D-type retroviruses (including Mason-Pfizer ape virus) or lentiviruses (including human immunodeficiency virus I). These retroviruses all show a genetically preserved structure with regard to the PBS sequence followed by SD and packaging signal, and they are therefore suitable for the insertion according to the invention of the [FS1] with a downstream intron.

A further subject of the present invention is an infectious virus particle which contains the retroviral vector according to the invention.

For the expression of the proteins coded by [FS1], [FS2] and/or [FS3], the vector can be introduced into a host cell which expresses the desired protein upon cultivation under suitable conditions. A further subject of the invention is thus host cells which are infected with the vector according to the invention and/or with the infectious virus particles named. The host cells are preferably lymphatic, haematopoietic or mesenchymal cells.

The retroviral vector of the present invention can be used universally. Possible fields of use are gene therapy, the cloning of genes or the expression and/or super-expression of proteins or RNA. Furthermore, the vector is particularly suitable for the transfection of lymphatic, haematopoietic or mesenchymal cells.

The present invention furthermore relates to a process for obtaining proteins in which a previously named host cell is cultivated in a suitable medium under conditions which are necessary for the expression of proteins coded by the foreign sequences [FS1], [FS2] and/or [FS3], the thus-produced protein being separated from the cells and the medium.

The retroviral vector can also be used within the framework of gene therapy or for the production of a pharmaceutical preparation for gene therapy, the vector being present in suitable form in order to be introduced into the target cells.

A further subject of the invention is a pharmaceutical preparation which contains a previously named vector together with pharmaceutically compatible auxiliaries and carriers. This preparation serves for the transfection of corresponding target cells in vitro and in vivo. Within the framework of the gene-therapeutic regime, lymphatic, haematopoietic or mesenchymal cells transfected with the vector (in vitro)can also be regarded and applied as a pharmaceutical preparation.

The experiments carried out within the framework of the present invention have shown that the foreign sequence 1 (FS1) can be inserted while retaining the genetic stability of the retroviral vector. Through the insertion according to the invention of the foreign sequence 1, a variety of novel configuration possibilities of retroviral vectors result. Some examples of how the incorporation according to the invention of an FS1 between PBS and SD broadens the configuration possibilities of retroviral vectors are listed in the following.

While retaining the enhancer/promoter in the LTR, a cDNA can be inserted as FS1. The FS2 can then contain a second expression cassette. The linking of the expression with FS2 can then either take place through an internal promoter or an internal ribosomal entry site in front of the cDNA in FS2. Thus the possibility of the simultaneous expression of several cDNAs from one vector is improved.

It is also possible to use in the FS1 a pure enhancer sequence which has an expression-promoting effect either on a promoter in the LTR (FS3) or on an internal promoter in FS2.

The insertion of a matrix-attachment region in the FS1 can have an expression-promoting effect on the expression of a vector which carries an internal promoter with following cDNA in the FS2 or a combination of promoter and cDNA as FS3 in the LTR.

If a vector is present which carries a promoter together with following cDNA as FS3 in the LTR, the incorporation of an RNA processing signal (e.g. post-transcriptional regulator element of the Woodchuck hepatitis virus) in the FS2 can have an expression-promoting effect, similar to that shown for conventional vectors (Zufferey et al., 1999).

The present invention is explained in the following using examples, figures and a sequence protocol.

EXAMPLES

Example 1

Preparation of a Vector According to the Invention

1. Original Construct

Figure 1A:
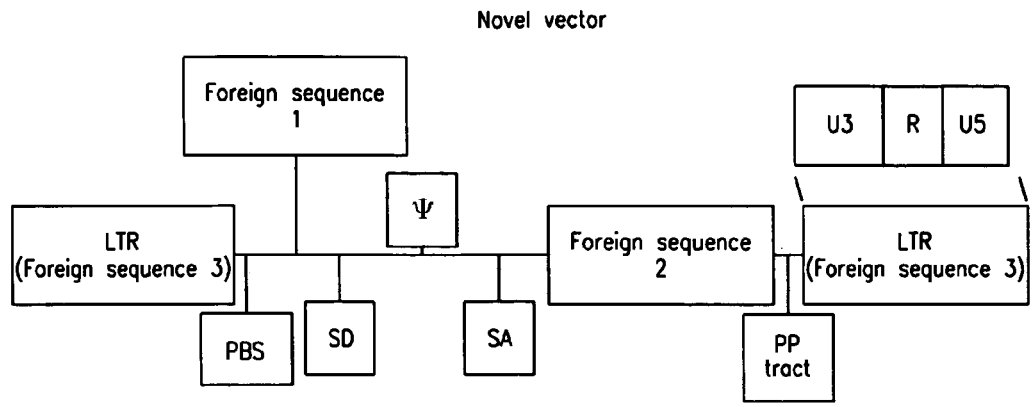
FIG. 1: Vector principle according to the invention compared with the structure of conventional vectors. The vector elements long terminal repeat (LTR), primer binding site (PBS), packaging signal (Ψ) and polypurine tract (PP tract) are obligatory. The LTR sequence is divided into the regions U3, R and U5. The presence of the splice donor (SD) and the splice acceptor is helpful but not absolutely necessary.
Figure 1B:
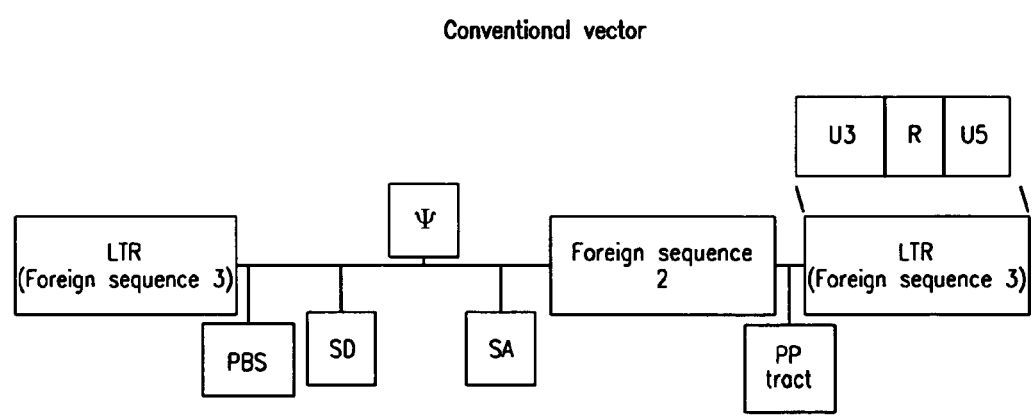
Figure 2:
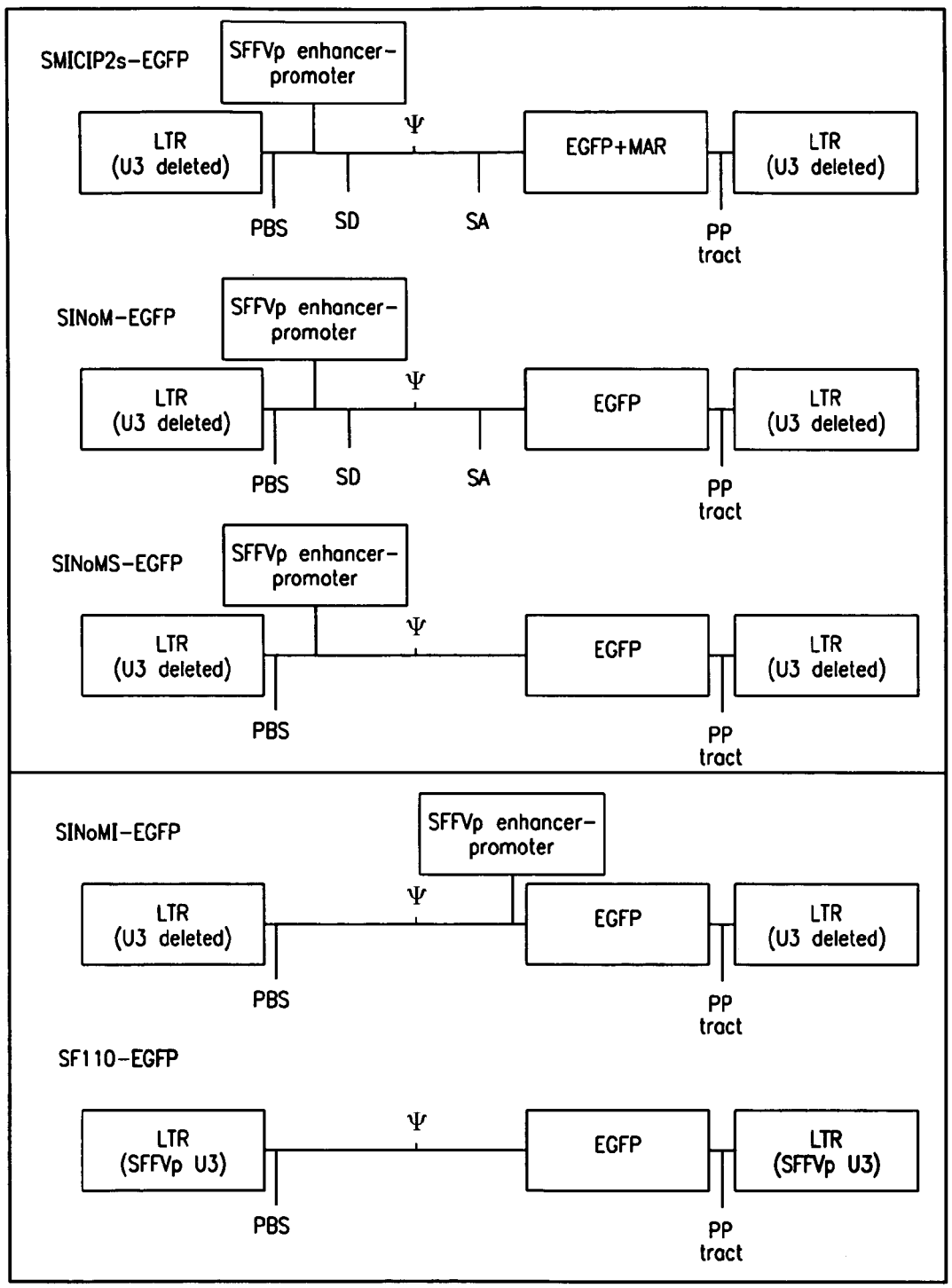
FIG. 2: Version according to the invention of the novel vector structure taking as an example SMICIP2s, associated variants SINoM-EGFP and SINoMS-EGFP and control vectors SINoMI-EGFP and SF110-EGFP.
Figure 3:
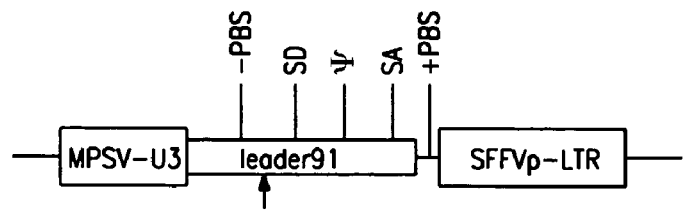
FIG. 3: Schematic overview of the sequence elements in pSFβ91; arrow: SalI restriction site.

The molecular-biological construction of the retroviral vector took place at the level of bacterial plasmids which contain the proviral sequences. The initial construct used here derives from the plasmid pSFβ91 (Hildinger et al., 1999; FIG. 3) which contains the 3' LTR from the spleen focus-forming virus (SFFVp), the 5' U3 from the MPSV and the 5'-untranslated region (leader) of the murine embryonic stem cell virus (MESV). pSFβ91 contains a modified leader region which is characterized by the presence of two splice signals, namely the splice donor (SD) and the splice acceptor (SA; FIG. 3).

Recognition sites for the restriction endonucleases NotI, EcoRI, BamHI and HindIII are located at the 3' end of the leader region. Compared with these plasmids from Hildinger et al. (1999), the constructs used also have a SalI-restriction site downstream of the PBS at base position 1030 (FIG. 3, arrow).

In the following, the cDNA of the enhanced green fluorescent protein (eGFP) and an 800-bp fragment of the core-matrix attachment region from the human β-interferon gene locus were introduced into these plasmids. Furthermore, the cis-active elements of the U3 region in the 3' LTR were deleted and the eGFP-cDNA placed under the transcriptional control of the U3 region of the SFFVp which was inserted into the leader region 5'-wards from the SD.

2. Insertion of the eGFP-cDNA

Figure 4:
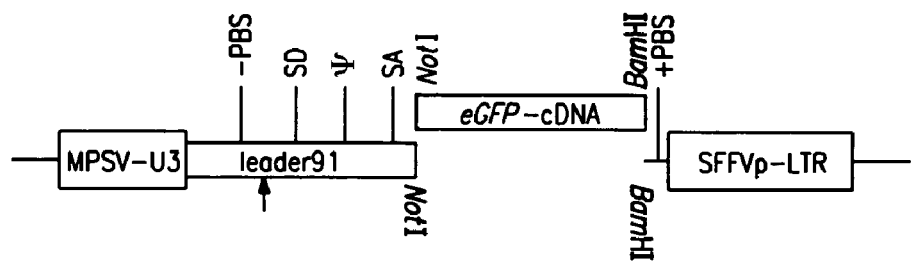
FIG. 4: Schematic representation of the insertion of eGFP-cDNA via the restriction sites NitI and BamHI into the plasmid pSFβ91.

The eGFP-cDNA from the plasmid pMP110(eGFP) (Schambach et al., 2000) in pSFβ91 was inserted via the restriction sites of NotI and BamHI at 5' end of the leader region (FIG. 4). The plasmid pSFβ91(eGFP) formed.

3. Deletion of the Cis-active Elements of the U3 Region in 3' LTR

Figure 5:
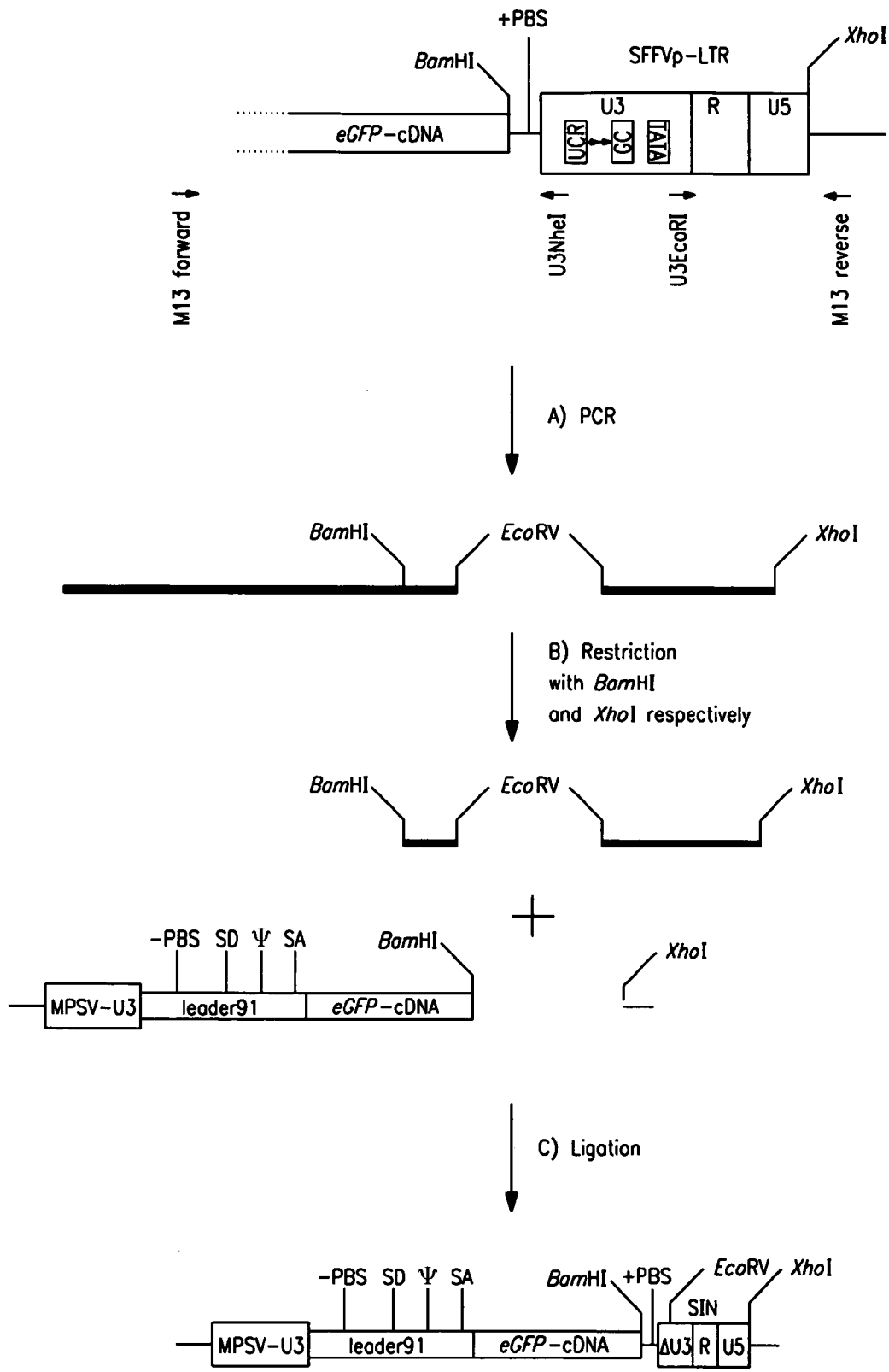
FIG. 5: Schematic overview of the procedure when deleting the U3 region in the 3' LTR of the plasmid pSFβ91 (eGFP).

For the deletion of the cis-active elements in the U3 region of the 3' LTR, two fragments from the plasmid pSFβ91(eGFP) were amplified via PCR (FIG. 5A). One fragment represents the section between the 5' end of the 5' LTR and the 5' end of the 3' LTR. The oligonucleotide M13forward served as primer for the forward-strand synthesis, and the oligonucleotide U3NheI for the synthesis of the reverse strand. U3NheI has restriction sites for NheI at the 5' end so that the amplified fragment also had this cleavage site at 3' end. After restriction of the amplified fragment with the enzyme BamHI, an 80-bp fragment remained that included the 5' end of the U3 region and the PP (FIG. 5B, +PBS).

The primers M13reverse (reverse-strand synthesis) and U3EcoRI (forward-strand synthesis) served for the amplification of the other fragment. They hybridize in sequence-specific manner at the 3' end of the U3 region (U3EcoRI) and downstream of the 3' LTR (M13reverse; FIG. 5A). Through U3EcoRI, which has an EcoRI restriction site at the 5' end, an EcoRI cleavage site was inserted at the 5' end of the amplified fragment. By restricting the amplified fragment with XhoI, a 170-bp fragment formed which, along with the 3' end of the U3 region, contained the R and U5 regions (FIG. 5B).

The two cut amplified fragments were inserted successively into the cloning vector pBluescript SK II via the restriction sites BamHI and EcoRV and EcoRV and XhoI respectively, to then be cut out as a fragment by means of the restriction enzymes BamHI and XhoI. The oligonucleotides U3NheI and U3EcoRI each terminate at the 5' end in base triplet ATC, so that an EcoRV cleavage site formed upon blunt-end linking of two cut amplified fragments (FIG. 5; sequence: GATATC).

Procedure for the PCR

Formulation: 10 ng DNA
1 μl Pfu Turbo™ polymerase (1 U/μl) (Manufacturer: Stratagene, La Jolla, US)
100 pmol primer 1
100 pmol primer 2
5 μl dNTP-Mix (10 mM each) (Manufacturer: Qiagen, Hilden DE)
5 μl 10×cloned-Pfu buffer (100 mM KCl; 100 mM $(NH_4)_2SO_4$; 200 mM Tris-HCl, pH 8.5; MM $MgSO_4$; 1% w/v Triton X-100; 1 mg/ml BSA) (Stratagene) ad.
50 μl distilled water.

The following programme was chosen on the Thermo-Cycler (Biometra, Göttingen):

| | | |
|---|---|---|
| Initial denaturation: | 60 s, 94° C. | |
| Denaturation: | 30 s, 94° C. | |
| Hybridization: | 30 s, 50° C.[1] | |
| Polymerization: | 60 s[2], 75° C. | 24 cycles |
| Last synthesis step: | 300 s, 75° C. | |
| Number of cycles: | 25 | |

[1] depending on the composition of the primers

[2] depending on the length of the fragments

A batch with only one of each of the two primers and a batch without primer served as negative controls for the PCR. For the positive control, a defined plasmid with special primers was used which delivers an amplification product of known size upon successful execution of the PCR.

The oligonucleotide primers used for the PCR were manufactured by Gibco BRL. The primers are shown below (SEQ ID NOS:2–7, respectively).

| Printer | Sequence (5'—3') | Use |
|---|---|---|
| M13 forward | TGACCGGCAGCAAAATG | Sequencing/PCR |
| M13 reverse | GGAAACAGCTATGACCATG | Sequencing/PCR |
| SalEagSF63 | GTCGACCGGCCGACTCAGTCAATCGG | PCR |
| U3EcoRI | ATCGAATTCACAACCCCTCACTCGGCGCGCCA | PCR |
| U3NheI | ATCGCTAGCGGTGGGGTCTTTCATTCCCCCCT | PCR |
| XhoEagSF65 | CTCGAGCGGCCGCTAGCTGCAGTAACGC | PCR |

The section downstream of the eGFP-cDNA was cut out of the plasmid pSFβ91(eGFP) with BamHI and XhoI and replaced by the PCR fragments linked together (FIG. 5C). The resultant plasmids pSIN91(eGFP) and pSIN110(eGFP) respectively contain no enhancer or promoter elements in the U3 region of the 3' LTR.

4. Insertion of the Promoter

Figure 6:
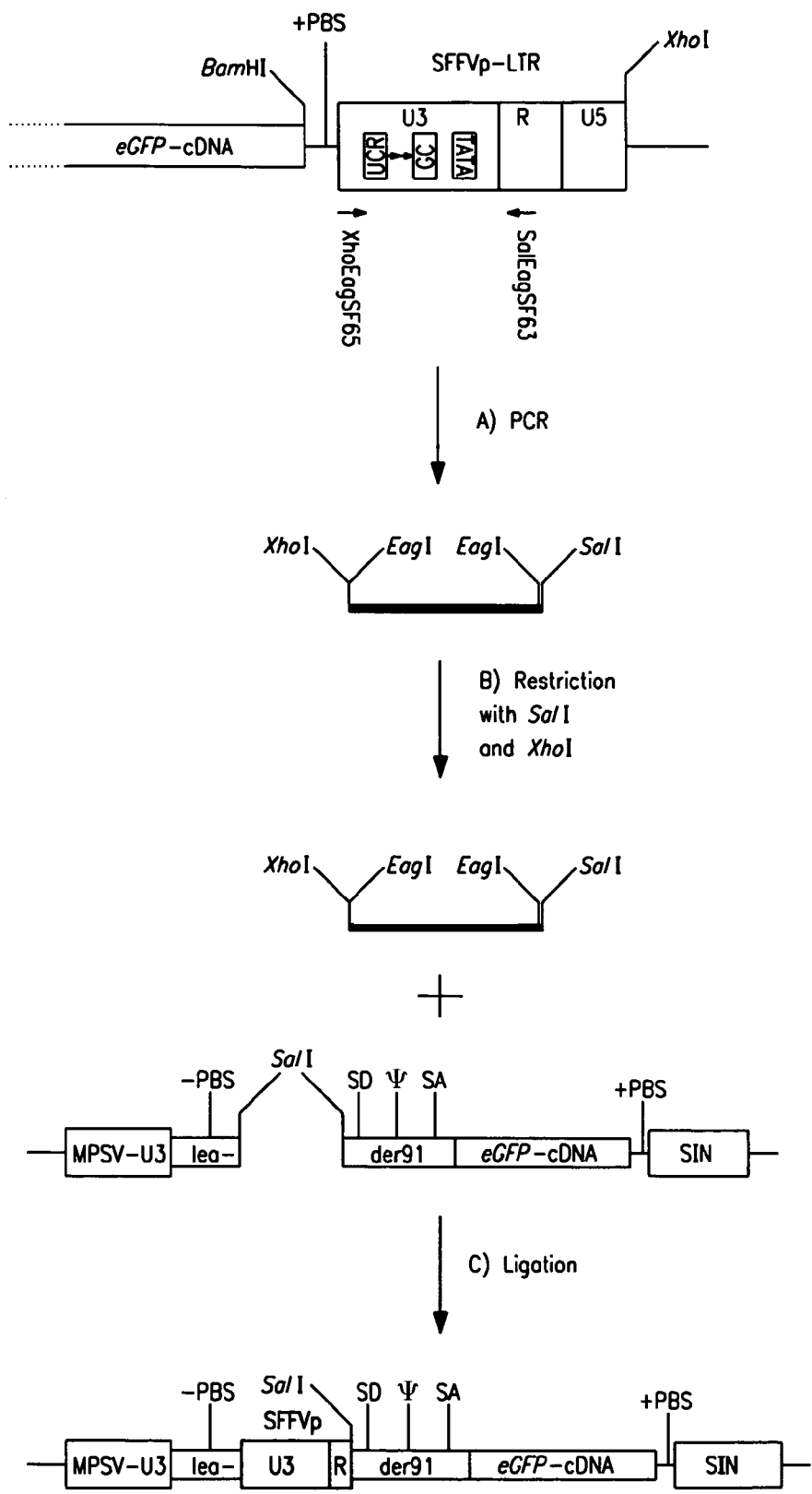
FIG. 6: Schematic overview of the amplification and insertion of the promoter region of SFFVp into the leader region of the plasmid pSIN91 (eGFP).
Figure 7:
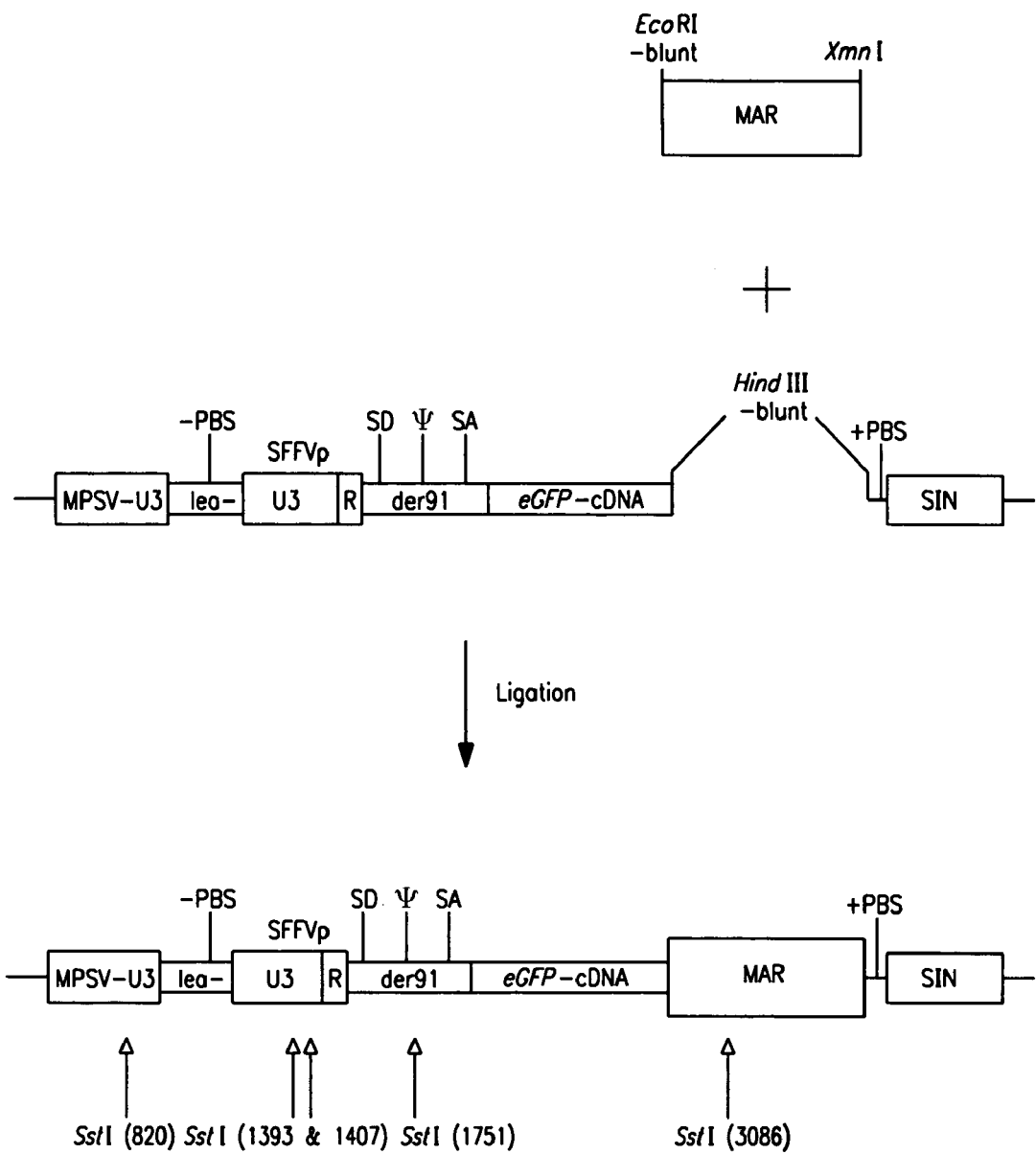
FIG. 7: Schematic overview of the insertion of the core-attachment region from the human interferon-β gene locus.

After the cis-active sequences have been deleted in the 3' LTR, the insertion of the promoter took place in the leader region via the SalI restriction site in front of the SD site (FIG. 6). The promoter fragment was first amplified via PCR with the sequence-specific primers XhoEagSF95 and SalEagSF63 which hybridize respectively at the 5' end of the 3' SFFV PLTRs (XhoEagSF65) and in the section approx 30 bp downstream of the 5' end of the R region (SalEagSF63) (FIG. 6A). The amplified fragment therefore also comprises, along with the entire U3 region, the first 27 nucleotides of the R region, which contain the Cap-Signal and are therefore indispensable for an optimal translation of mRNA (Cupelli and Lenz, 1991).

The oligonucleotides used for the PCR contain recognition sites for, respectively, the restriction endonucleases XhoI and EagI (XhoEagSF65) and SalI and EagI (SalEagSF63) at their 5' end, so that the amplified fragment carries precisely these cleavage sites at the 5' and 3' end respectively. In order to insert the PCR product into the vector via the SalI restriction site, it was cut beforehand with XhoI and SalI (FIG. 6B). Due to the complementarity of the base overhangs of XhoI and SalI after a restriction, this process is possible. Thanks to the primer design, a SalI restriction site was reproduced on only one side each time after the ligation (FIG. 6C) and can be re-used during future clonings for the insertion of further fragments without again cutting out the promoter.

5. Insertion of the Core Matrix-attachment Region (MAR)

An approx. 800-bp fragment of the core matrix-attachment region from the human interferon-β gene locus was cut out of the plasmid pTZE20 (Mielke et al., 1990) by means of the restriction endonucleases XmnI and EcoRI. By means of the Klenow polymerase, the four-nucleotide-sized base overhang of the EcoRI cleavage site was filled up to a blunt end, so that the restriction fragment had blunt ends on both flanks. The MAR was inserted directly at the 3' end of the eGFP cDNA via the HindIII cleavage site, the base overhangs of which were also filled up to blunt ends with the Klenow fragment of the DNA polymerase I of E. coli after the cut. The MAR was inserted into the vector in sense orientation to the promoter, which was verified by a restriction cleavage with the endonuclease SstI, which cuts the MAR into two differently-sized fragments. It thus lies in the same orientation to the promoter as in the human interferon-β gene locus (Mielke et al., 1990).

Figure 8:
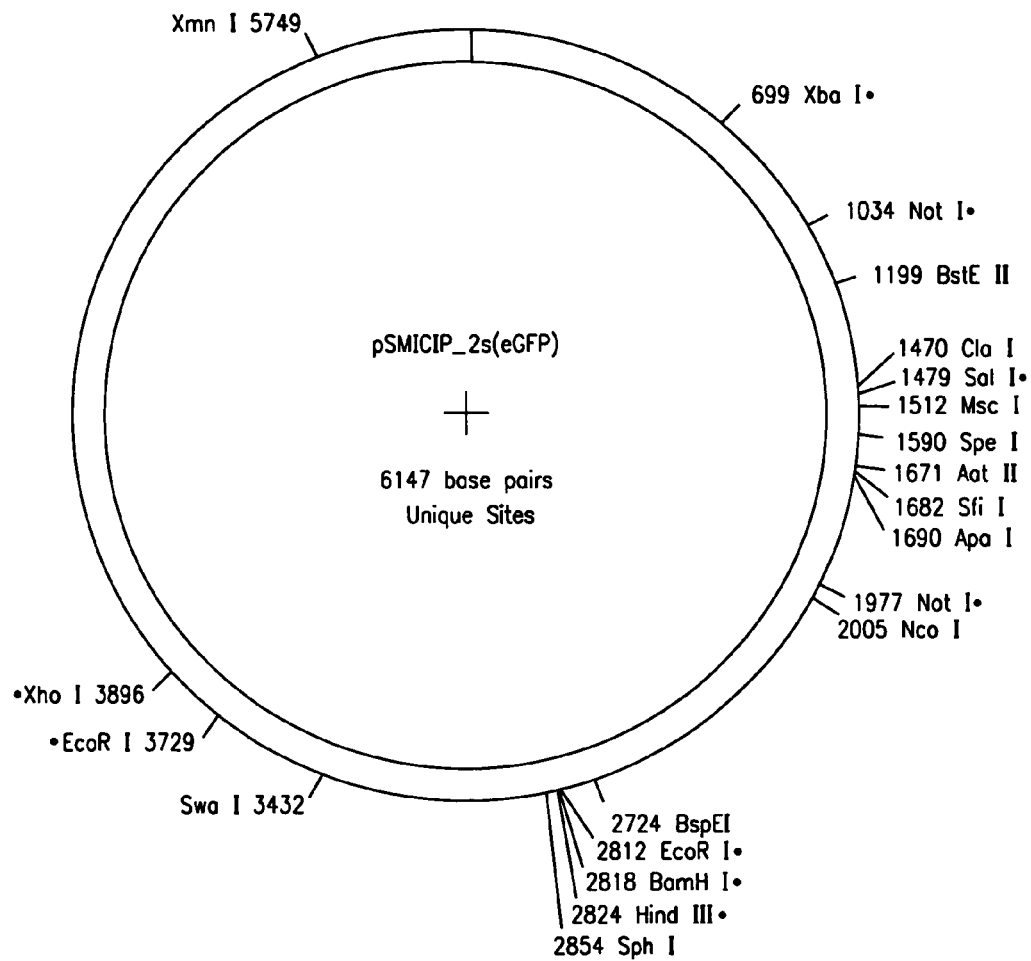
FIG. 8: Plasmid map of pSMICIP2s-eGFP.

The proviral plasmid pSMICIP2s(eGFP) was obtained, the plasmid map of which is shown in FIG. 8. A specimen of this plasmid was deposited on the Aug. 31, 2000 at the Deutsche Sammlung von Mikroorganismen und Zellkulturen (DSMZ), Mascheroder Weg 1b, 38124 Brunswick, under the No. DSM 13711.

Example 2

Evaluation of the Packaging Efficiency and Expression Properties

The following experiments were carried out to examine whether the insertion according to the invention of the foreign sequence 1 [FS1]

A) is possible while retaining the packaging efficiency and

B) allows an improvement of the expression properties.

A) Retaining the Packaging Efficiency

Background: Replication defects of retroviral vectors are prepared in the cell culture in safety-modified packaging cells. A common packaging cell is PHOENIX-ampho, which releases the replication-defective mouse retroviruses with amphotropic envelope proteins (Kinsella and Nolan, 1996). Up to 96 hours after transfection of the proviral vector plasmids, virus supernatants with an infectious titre of between $10^5$ and $10^6$ particles per ml cell culture supernatant can be harvested. As previously described (Fehse et al., 2000), a second plasmid is cotransfected, which codes for the envelope protein of the vesicular stomatitis virus (VSV-G). Thus, mixed virus envelopes with a broadened host range can be produced, the subsequent transduction of various cell types being facilitated. This modification has no influence on the genetic properties of the transferred vector (Laer et al., 1998). The decisive factors for the retaining of the packaging efficiency are the size and the genetic stability of the vector genome as well as the absence of an interference with the function of ψ. According to the state of research, it was unknown whether foreign sequences can be inserted in the highly-preserved region between PBS and SD without adversely affecting the RNA secondary structure necessary for the packaging (Alford et al., 1991).

Procedure: The above-mentioned plasmids were introduced with the calcium phosphate transfection method together with a VSV-G protein-coding plasmid into a uniform lawn of PHOENIX-ampho cells. Within the next 96 hours, cell culture supernatants were removed by fractination, filtered (0.22 µm) and preserved in aliquots at −70° C. The infectious virus particles content was measured by retroviral transduction of mesenchymal mouse fibroblasts of the line SC1, by reacting a constant target cell count with increasing quantities of virus-containing supernatant (Fehse et al, 2000). The fraction of the successfully retrovirally transduced cells was measured after 48 hours via the expression of EGFP in the flow cytometer. The maximum virus titre was established using the average of the best five results.

Result: The titres of the vectors SMICIP2s (eGFP) (titre 223800±45400/ml) and SINoMI-EGFP (titre 237500±55000/ml) are of the same order as the titre of the conventional vector SF110-EGFP (titre 134700±76700/ml). The vectors SINoM (43500±13000/ml) and SINoMS (31800±64000/ml) achieve lower titres.

Appraisal: These experiments show that the influence of the foreign sequence 1 [FS1] on the titre is context-dependent, i.e. also depends on the structure of the [FS2] and [FS3]. Standard titres can be achieved in combination with the MAR in the foreign sequence 2 [FS2]. Control experiments show that the MAR sequences per se do not increase the titre. The achievement of sufficient virus titres is therefore also possible with the vector structure according to the invention in other sequence combinations.

B) Expression Properties

Background: The expression of the transferred genes is an important criterion for the appraisal of the quality of retroviral vectors. For the expression of many transgenes, it is beneficial, for some even decisive, to place an intron in the 5' untranslated region (Buchmann and Berg, 1988; Hildinger et al., 1999). The intron must however be retained in the packaging cell upon the expression of the retroviral RNA, as it is otherwise no longer contained in the transferred retroviral genome. Retention of the intron can for example be achieved by inserting splice donor and splice acceptor signals at the flanks of Ψ (Hildinger et al., 1999). To date, this has been practised only with vectors which carry enhancer-promoter sequences in the LTRs. Such vectors have the potential disadvantage that the transcriptional activation of downstream cellular sequences can result if the enhancer-promoter is activated in the 3' LTR. Therefore, it is desirable to convert the principle of the intron-containing transgene in the context of a vector the enhancer-promoter region of which was deleted in the LTR (so-called self-inactivating vector, Yu et al., 1986). Such a construction was realized for the first time in the vectors SMICIP2s(eGFP) and SINoM-EGFP according to the invention.

Procedure: To examine the expression properties of the SMCIP2s-EGFP vector, mouse fibroblasts of the line SC1 and mouse lymphocytes of the line EL4 were transduced, using the same quantities of infectious virus particles each time. The expression level of EGFP was measured after 48 hours in the flow cytometer. At least 10,000 independent events were measured per recording. The average expression level was ascertained using the average (average fluorescence in arbitrary units) from at least two independent experiments.

Result: In SC1 cells, the vector SMICIP2s (eGFP) brings about the highest expression (average fluorescence 682±19) of all tested vectors. SINoM-EGFP, the variant without MAR, is lower (475±21). SINoMS-EGFP, the variant without intron and MAR, achieves an even lower expression (183±11) and is in this respect identical to the conventional vector, SF110-EGFP (185±2). The control vector SINoMI-EGFP corresponds to the standard structure of a self-inactivating vector, as the promoter without intron lies directly in front of the cDNA; this vector is, in terms of the expression, also inferior to the vector SMICIP2s (eGFP) (315±21).

Also in EL4 cells, the vectors according to the invention with the enhancer-promoter as foreign sequence 1 [FS1] and downstream intron bring about the highest expression but there is no beneficial influence of the MAR region; the vector SINoM-EGFP brings about the highest expression (713±19), followed by SMICIP2s(eGFP) (600±14). SINoMS-EGFP, the variant without intron and MAR, achieves a clearly lower expression (391±2), but is still better than the conventional vector SF110-EGFP (185±2). The control SINoMI-EGFP (391±2) proves again to be inferior to the vectors SMICIP2s (eGFP) and SINoM-EGFP.

Appraisal: These experiments show that the insertion according to the invention of foreign sequences between PBS and SD can be used to improve the expression properties of retroviral vectors. The chosen configuration of the enhancer promoter directly upstream of the retroviral intron combines the safety-relevant advantages of a self-inactivating vector (with deleted enhancer-promoter sequences of the LTR) with the expression-promoting properties of an intron-containing vector. The gain in expression by a factor of 2 to 3 compared with conventional vector types is seen in both cell lines. The presence of the MAR region, on the other hand, was beneficial only in the examined fibroblasts, which indicates a pronounced differentiation dependency of this element. These findings underline that the expression gain achieved through the novel vector structure does not depend on the presence of a MAR.

C) Summary Appraisal:

The vector structure chosen according to the invention broadens the possibilities of the construction of retro-viral gene transfer vectors. It was shown by means of experiments that a foreign gene insertion between the retroviral PBS and the packaging signal is possible vectors with this structures can be produced in sufficient titres in a preferred version the foreign sequence insertion can be used to produce vectors with improved expression properties and advantageous properties which potentially promote the biological safety of the gene transfer.

REFERENCES

ALFORD, R. L., HONDA, S., and BELMONT, J. W. (1991). RNA secondary structure of the packaging signal for Moloney murine leukemia virus. Virology 183, 611–619.

BAUM, C., HEGEWISCH-BECKER, S., ECKERT, H.-G., STOCKING, C., and OSTERTAG, W. (1995). Novel retroviral vectors for efficient expression of the multidrug-resistance (mdr-l) gene in early hemopoietic cells. J. Virol. 69, 7541–7549.

BUCHMAN, A. R. and BERG, P. (1988). Comparison of intron-dependent gene expression. Mol. Cell. Biol. 8, 4395–4405.

DEFFAUD, C. and DARLIX, J. L. (2000). Characterization of an internal ribosomal entry segment in the 5' leader of murine leukemia virus env RNA. J. Virol. 74, 846–850.

FEHSE, B., RICHTERS, A., PUTIMTSEVA-SCHARF, K., KLUMP, H., LI, Z., OSTERTAG, W., ZANDER, A. R., and BAUM, C. (2000). CD34 splice-variant: an attractive marker for selection of gene-modified cells. Mol. Ther. 5, 448–456.

HILDINGER, M., ABEL, K. L., OSTERTAG, W., and BAUM, C. (1999). Design of 5′ untranslated sequences in retroviral vectors developed for medical use. J. Virol. 73, 4083–4089.

KINSELLA, T. M., and NOLAN, G. P. (1996). Episomal vectors rapidly and stably produce high-titer recombinant retrovirus. Hum. Gene Ther. 7, 1405–1413.

VON LAER, D., THOMSEN, S., VOGT, B., DONATH, M., KRUPPA, J., REIN, A., OSTERTAG, W., and STOCKING, C. (1998). Entry of amphotropic and 10A1 pseudotyped murine retroviruses is restricted in hematopoietic stem cell lines. J. Virol. 72, 1424–1430.

SCHAMBACH, A., WODRICH, H., HILDINGER, M., BOHNE, J., KRAUESSLICH, H. G., BAUM, C. (2000). Context-dependence of different modules for post-transcriptional enhancement of gene expression from retroviral vectors. Mol. Ther., 2: 435–445.

SCHÜBELER, D., MIELKE, C., MAASS, K., and BODE, J., (1996) . Scaffold/matrix-attachment regions act upon transcription in a context-dependent manner. Biochemistry 35, 11160–11169.

YANG, T. T., CHENG, L., and KAIN, S. R. (1996). Optimized codon usage and chromophore mutations provide enhanced sensitivity with the green fluorescent protein. Nucleic Acids Res. 24, 4592–4593.

YU, S. F., VON RUDEN, T., KANTOFF, P. W., GARBER, C., SEIBERG, M., RUTHER, U., ANDERSON, W. F.; WAGNER, E. F., and GILBOA, E. (1986) Self-inactivating retroviral vectors designed for transfer of whole genes into mammalian cells. Proc Natl Acad Sci USA 83:3194–3198.

ZUFFEREY, R., DONELLO, J. E., TRONO, D., and HOPE, T. J. (1999). Woodchuck hepatitis virus post-transcriptional regulatory element enhances expression of transgenes delivered by retroviral vectors. J. Virol. 73, 2886–2892.

The invention claimed is:

1. A composition of matter comprising an isolated retroviral murine embryonic stem cell virus (MESV) vector comprising the following components obtained from a MESV, wherein said components are set forth in the following 5' to 3' order:
   a terminal sequence repeat (long terminal repeat, LTR);
   the retroviral primer binding site;
   the retroviral splice donor signal;
   the retroviral packaging signal;
   an optional retroviral splice acceptor signal; and
   a polypurine tract (PP tract);
   wherein the vector further comprises a foreign sequence 1 located between the retroviral primer binding site and the retroviral splice donor, wherein foreign sequence 1 is selected from the group consisting of an enhancer-promoter sequence, an enhancer sequence, a cDNA sequence, a sequence for chromatin-modification, and a sequence for RNA processing signals.

2. A composition of matter comprising an isolated retroviral murine embryonic stem cell virus (MESV) vector comprising the following components obtained from a MESV, wherein said components are set forth in the following 5' to 3' order:
   a terminal sequence repeat (long terminal repeat, LTR);
   the retroviral primer binding site;
   the retroviral splice donor signal;
   the retroviral packaging signal;
   the retroviral splice acceptor signal; and
   a polypurine tract;
   wherein the vector further comprises a foreign sequence 1 located between the retroviral primer binding site and the retroviral splice donor, wherein foreign sequence 1 is selected from the group consisting of an enhancer-promoter sequence, an enhancer sequence, a cDNA sequence, a sequence for chromatin-modification, and a sequence for RNA processing signals, and further comprising a foreign sequence 2 inserted between the retroviral splice acceptor signal and the polypurine tract, wherein foreign sequence 2 is selected from the group consisting of a cDNA sequence, an enhancer sequence, a promoter sequence, a sequence for internal ribosomal entry sites (IRES), a sequence for chromatin-modification, and a sequence for RNA processing signals.

3. A composition of matter comprising an isolated retroviral murine embryonic stem cell virus (MESV) vector comprising the following components obtained from a MESV, wherein said components are set forth in the following 5' to 3' order:
   a terminal sequence repeat (long terminal repeat, LTR);
   the retroviral primer binding site;
   the retroviral splice donor signal;
   the retroviral packaging signal;
   an optional retroviral splice acceptor signal; and
   a polypurine tract (PP tract);
   wherein the vector further comprises a foreign sequence 1 located between the retroviral primer binding site and the retroviral splice donor, wherein foreign sequence 1 is selected from the group consisting of an enhancer-promoter sequence, an enhancer sequence, a cDNA sequence, a sequence for chromatin-modification, and a sequence for RNA processing signals, and
   wherein at least one terminal sequence repeat (LTR) contains a foreign sequence 3 selected from the group consisting of a cloning site for the deletion of the LTR-enhancer promoter, an enhancer sequence, a promoter sequence, a cDNA sequence, a sequence for chromatin-modification, and a sequence for RNA processing signals.

4. A composition of matter comprising a DNA comprising SEQ ID NO: 1.

5. The composition of claim 1, 2, or 3, wherein the retroviral splice donor signal is inactivated by mutation.

6. The composition of claim 1, 2, or 3, wherein the retroviral splice acceptor signal is present, but inactivated by mutation.

7. A pharmaceutical preparation, comprising the composition of claim 1, 2, 3 or 4, and further comprising a pharmaceutically compatible auxiliary.

8. The pharmaceutical preparation of claim 7, further comprising a carrier substance.

9. A composition of matter comprising a host cell, wherein the host cell is transfected with the composition of claim 1, 2, 3 or 4.

10. The composition of claim 9, wherein the cell is selected from the group consisting of a hematopoietic cell, a mesenchymal cell, and a lymphatic cell.

11. The composition of matter of claim 1, 2, or 3, wherein the retroviral vector is infectious.

12. A composition of matter comprising a host cell comprising the composition of claim 11.

13. The composition of claim 12, wherein the host cell is selected from the group consisting of a hematopoietic cell, a mesenchymal cell, and a lymphatic cell.

14. A method for obtaining proteins, comprising the steps of
    (a) cultivating a host cell transfected with the composition of claim 1, 2, 3 or 4 in a suitable medium under conditions that are required to express proteins encoded by a foreign sequence, whereby proteins encoded by the foreign sequence are expressed; and
    (b) separating the expressed proteins away from the cells and the medium.

15. The method of claim 14, wherein the protein being expressed is encoded by foreign sequence 1.

16. The method of claim 14, wherein the proteins being expressed are encoded by foreign sequence 1 and foreign sequence 2.

17. The method of claim 14, wherein the proteins being expressed are encoded by foreign sequence 1 and foreign sequence 3.

18. A method for obtaining proteins, comprising the steps of
  (a) cultivating a host cell comprising an infectious viral composition of claim 1, 2, or 3 in a suitable medium under conditions that are required to express proteins encoded by a foreign sequence, whereby proteins encoded by the foreign sequence are expressed; and
  (b) separating the expressed proteins away from the cells and the medium.

19. The method of claim 18, wherein the protein being expressed is encoded by foreign sequence 1.

20. The method of claim 18, wherein the proteins being expressed are encoded by foreign sequence 1 and foreign sequence 2.

21. The method of claim 18, wherein the proteins being expressed are encoded by foreign sequence 1 and foreign sequence 3.

22. The composition of claim 1, wherein foreign sequence 1 is an enhancer-promoter sequence.

23. The composition of claim 1, wherein foreign sequence 1 is an enhancer sequence.

24. The composition of claim 1, wherein foreign sequence 1 is a cDNA sequence.

25. The composition of claim 1, wherein foreign sequence 1 is a sequence for chromatin-modification.

26. The composition of claim 1, wherein foreign sequence 1 is a sequence for RNA processing signals.

27. The composition of claim 2, wherein foreign sequence 1 is an enhancer-promoter sequence.

28. The composition of claim 2, wherein foreign sequence 1 is an enhancer sequence.

29. The composition of claim 2, wherein foreign sequence 1 is a cDNA sequence.

30. The composition of claim 2, wherein foreign sequence 1 is a sequence for chromatin-modification.

31. The composition of claim 2, wherein foreign sequence 1 is a sequence for RNA processing signals.

32. The composition of claim 3, wherein foreign sequence 1 is an enhancer-promoter sequence.

33. The composition of claim 3, wherein foreign sequence 1 is an enhancer sequence.

34. The composition of claim 3, wherein foreign sequence 1 is a cDNA sequence.

35. The composition of claim 3, wherein foreign sequence 1 is a sequence for chromatin-modification.

36. The composition of claim 3, wherein foreign sequence 1 is a sequence for RNA processing signals.

37. The composition of claim 2, wherein foreign sequence 2 is a cDNA sequence.

38. The composition of claim 2, wherein foreign sequence 2 is an enhancer sequence.

39. The composition of claim 2, wherein foreign sequence 2 is a promoter sequence.

40. The composition of claim 2, wherein foreign sequence 2 is a sequence for internal ribosomal entry sites (IRES).

41. The composition of claim 2, wherein foreign sequence 2 is a sequence for chromatin-modification.

42. The composition of claim 2, wherein foreign sequence 2 is a sequence for RNA processing signals.

43. The composition of claim 3, wherein foreign sequence 3 is a cloning site for the deletion of the LTR-enhancer promoter.

44. The composition of claim 3, wherein foreign sequence 3 is an enhancer sequence.

45. The composition of claim 3, wherein foreign sequence 3 is a promoter sequence.

46. The composition of claim 3, wherein foreign sequence 3 is a cDNA sequence.

47. The composition of claim 3, wherein foreign sequence 3 is a sequence for chromatin-modification.

48. The composition of claim 3, wherein foreign sequence 3 is and a sequence for RNA processing signals.

49. The composition of claim 10, wherein the cell is a hematopoietic cell.

50. The composition of claim 10, wherein the cell is a mesenchymal cell.

51. The composition of claim 10, wherein the cell is a lymphatic cell.

52. The composition of claim 13, wherein the cell is a hematopoietic cell.

53. The composition of claim 13, wherein the cell is a mesenchymal cell.

54. The composition of claim 13, wherein the cell is a lymphatic cell.

* * * * *

SEQUENCE LISTING

```
<160> NUMBER OF SEQ ID NOS: 7

<210> SEQ ID NO 1
<211> LENGTH: 6147
<212> TYPE: DNA
<213> ORGANISM: Artificial sequence
<220> FEATURE:
<223> OTHER INFORMATION: Description of the artificial sequence: Plasmid
      pSMICIP2s(eGFP)

<400> SEQUENCE: 1
ctgcctcgcg cgtttcggtg atgacggtga aaacctctga cacatgcagc tcccggagac      60
ggtcacagct tgtctgtaag cggatgccgg gagcagacaa gcccgtcagg gcgcgtcagc     120
gggtgttggc gggtgtcggg gcgcagccat gacccagtca cgtagcgata gttactatgc     180
ggcatcagag cagattgtac tgagagtgca ccatatgcgg tgtgaaatac cgcacagatg     240
cgtaaggaga aaataccgca tcaggcgcca ttcgccattc aggctgcgca actgttggga     300
agggcgatcg gtgcgggcct cttcgctatt acgccagctg gcgaaagggg gatgtgctgc     360 aagcgatta agttgggtaa cgccagggtt ttcccagtca cgacgttgta aaacgacggc     420
cagtgaatta gtactctagc ttaagtaagc cattttgcaa ggcatggaaa aatacataac     480
tgagaataga gaagttcaga tcaaggttag gaacagagag acaggagaat atgggccaaa     540
caggatatct gtggtaagca gttcctgccc cggctcaggg ccaagaacag ttggaacagc     600
agaatatggg ccaaacagga tatctgtggt aagcagttcc tgccccggct cagggccaag     660
aacagatggt ccccagatgc ggtcccgccc tcagcagttc tagagaacca tcagatgttt     720
ccagggtgcc ccaaggacct gaaatgaccc tgtgccttat ttgaactaac caatcagttc     780
gcttctcgct tctgttcgcg cgcttctgct ccccgagctc aataaaagag cccacaaccc     840
ctcactcggc gcgccagtcc tccgattgac tgagtcgccc gggtacccgt gttctcaata     900
aaccctcttg cagttcatc cgactcgtgg tctcgctgat ccttgggagg gtctcctcag     960
attgattgac tgcccacctc gggggtcttt catttggagg ttccaccgag atttggagac    1020
ccctgcccgt cgagcggccg ctagctgcag taacgccatt ttgcaaggca tggaaaaata    1080
ccaaaccaag aatagagaag ttcagatcaa gggcgggtac atgaaaatag ctaacgttgg    1140
```

-continued

```
gccaaacagg atatctgcgg tgagcagttt cggccccggc ccggggccaa gaacagatgg    1200
tcaccgcagt ttcggccccg gcccgaggcc aagaacagat ggtccccaga tatggcacaa    1260
ccctcagcag tttcttaaga cccatcagat gtttccaggc tcccccaagg acctgaaatg    1320
accctgcgcc ttatttgaat taaccaatca gcctgcttct cgcttctgtt cgcgcgcttc    1380
tgcttcccga gctctataaa agagctcaca cccctcact cggcgcgcca gtcctccgac    1440
agactgagtc ggccggtcga atcaagctca tcgataccgt cgaccaccga ccccccgcc    1500 gggaactaag ctggccagcg gtcgtttcgt gtctgtctct gtctttgtgc gtgtttgtgc    1560
cggcatctaa tgtttgcgcc tgcgtctgta ctagttggct aactagatct gtatctggcg    1620
gtcccgcgga agaactgacg agttcgtatt cccggccgca gccctggga gacgtcccag     1680 cggcctcggg ggcccgtttt gtggcccatt ctgtatcagt taacctaccc gagtcggact    1740
ttttggagct ccgccactgt ccgagggta cgtggctttg ttggggacg agagacagag      1800 acacttcccg cccccgtctg aatttttgct ttcggtttta cgccgaaacc gcgccgcgcg    1860
tcttgtctgc tgcagcatcg ttctgtgttg tctctgtctg actgtgtttc tgtatttgtc    1920
tgaaaattag ctcgacaaag ttaagtaata gtccctctct ccaagctcac ttacaggcgg    1980
ccgctctagc gctaccggtc gccaccatgg tgagcaaggg cgaggagctg ttcaccgggg    2040
tggtgcccat cctggtcgag ctggacggcg acgtaaacgg ccacaagttc agcgtgtccg    2100
gcgagggcga gggcgatgcc acctacggca agctgaccct gaagttcatc tgcaccaccg    2160
gcaagctgcc cgtgccctgg cccaccctcg tgaccaccct gacctacggc gtgcagtgct    2220
tcagccgcta ccccgaccac atgaagcagc acgacttctt caagtccgcc atgcccgaag    2280
gctacgtcca ggagcgcacc atcttcttca aggacgacgg caactacaag acccgcgccg    2340
aggtgaagtt cgagggcgac accctggtga accgcatcga gctgaagggc atcgacttca    2400
aggaggacgg caacatcctg ggcacaagc tggagtacaa ctacaacagc cacaacgtct     2460
atatcatggc cgacaagcag aagaacggca tcaaggtgaa cttcaagatc cgccacaaca    2520
tcgaggacgg cagcgtgcag ctcgccgacc actaccagca gaacacccc atcggcgacg     2580 gccccgtgct gctgcccgac aaccactacc tgagcaccca gtccgccctg agcaaagacc    2640
ccaacgagaa gcgcgatcac atggtcctgc tggagttcgt gaccgccgcc gggatcactc    2700
tcggcatgga cgagctgtac aagtccggac tcagatccag cgctgataac ccagcctcca    2760
ccacaaacaa ggatgccggt accggcgccc accaccacca ccaccacatg tgaattcgga    2820
tccaagcttt ttctctacac tgaagtcatg atggcatgct tctatattat tttctaaaag    2880
atttaaagtt ttgccttctc catttagact tataattcac tggaatttt ttgtgtgtat    2940 ggtatgacat atgggttccc ttttattttt tacatataaa tatatttccc tgttttcta     3000 aaaaagaaaa agatcatcat tttcccattg taaaatgcca tatttttttc ataggtcact    3060
tacatatatc aatgggtctg tttctgagct ctactctatt ttatcagcct cactgtctat    3120
ccccacacat ctcatgcttt gctctaaatc ttgatattta gtggaacatt ctttcccatt    3180
ttgttctaca agaatatttt ttgttaattg tcttttgggc ttcctatata cattttagaa    3240
tgaggttggc aagttaacaa acagcttttt tggggtgaac atattgacta caaatttatg    3300
tggaaagaaa gtataccttc acaatattaa gtcttttagt tcatgaatat agtatgtctc    3360
tccgtttctg cattaactta gacattcatt aatttctctc acaatttata agtttattta    3420
gatcttcatt catttaaatc ttcactaacc tctcatttac aatttgtaag ttttctgggt    3480
aacagtcttg cacttctttg cctagattta tttccaagta gattattttc atacatcgtc    3540
```

```
tatggtgtca ttttttaaaat gtaattttttc accttttttat tgctaaagag agatgactga    3600
ttgttaatat tgatcttgtg cgtggcgacc ttgctgaatt agcttaacac gagccataga    3660
tagaataaaa gattttatttt agtctccaga aaaggggggg aatgaaagac cccaccgcta    3720
gcgatatcga attcacaacc cctcactcgg cgcgccagtc ctccgacaga ctgagtcgcc    3780
cgggtacccg tgttctcaat aaaccctctt gcagttgcat ccgactcgtg gtctcgctgt    3840
tccttgggag ggtctcctct gagtgattga ctgcccacct cggggtcttt tcattctcga    3900
gagctttggc gtaatcatgg tcatagctgt ttcctgtgtg aaattgttat ccgctcacaa    3960
ttccacacaa catacgagcc ggaagcataa agtgtaaagc ctggggtgcc taatgagtga    4020
gctaactcac attaattgcg ttgcgctcac tgcccgcttt ccagtcggga aacctgtcgt    4080
gccagctgca ttaatgaatc ggccaacgcg cggggagagg cggtttgcgt attgggcgct    4140
cttccgcttc ctcgctcact gactcgctgc gctcggtcgt tcggctgcgg cgagcggtat    4200
cagctcactc aaaggcggta atacggttat ccacagaatc aggggataac gcaggaaaga    4260
acatgtgagc aaaaggccag caaaaggcca ggaaccgtaa aaaggccgcg ttgctggcgt    4320
ttttccatag gctccgcccc cctgacgagc atcacaaaaa tcgacgctca agtcagaggt    4380
ggcgaaaccc gacaggacta taaagatacc aggcgtttcc ccctggaagc tccctcgtgc    4440
gctctcctgt tccgaccctg ccgcttaccg gatacctgtc cgcctttctc ccttcgggaa    4500
gcgtggcgct ttctcaatgc tcacgctgta ggtatctcag ttcggtgtag gtcgttcgct    4560
ccaagctggg ctgtgtgcac gaaccccccg ttcagcccga ccgctgcgcc ttatccggta    4620
actatcgtct tgagtccaac ccggtaagac acgacttatc gccactggca gcagccactg    4680
gtaacaggat tagcagagcg aggtatgtag gcggtgctac agagttcttg aagtggtggc    4740
ctaactacgg ctacactaga aggacagtat ttggtatctg cgctctgctg aagccagtta    4800
ccttcggaaa aagagttggt agctcttgat ccggcaaaca aaccaccgct ggtagcggtg    4860
gtttttttgt ttgcaagcag cagattacgc gcagaaaaaa aggatctcaa gaagatcctt    4920
tgatcttttc tacggggtct gacgctcagt ggaacgaaaa ctcacgttaa gggattttgg    4980
tcatgagatt atcaaaaagg atcttcacct agatcctttt aaattaaaaa tgaagtttta    5040
aatcaatcta agtatatat gagtaaactt ggtctgacag ttaccaatgc ttaatcagtg    5100
aggcacctat ctcagcgatc tgtctatttc gttcatccat agttgcctga ctccccgtcg    5160
tgtagataac tacgatacgg gagggcttac catctggccc cagtgctgca atgataccgc    5220
gagacccacg ctcaccggct ccagatttat cagcaataaa ccagccagcc ggaagggccg    5280
agcgcagaag tggtcctgca actttatccg cctccatcca gtctattaat tgttgccggg    5340
aagctagagt aagtagttcg ccagttaata gtttgcgcaa cgttgttgcc attgctgctg    5400
gcatcgtggt gtcacgctcg tcgtttggta tggcttcatt cagctccggt tcccaacgat    5460
caaggcgagt tacatgatcc cccatgttgt gcaaaaaagc ggttagctcc ttcggtcctc    5520
cgatcgttgt cagaagtaag ttggccgcag tgttatcact catggttatg gcagcactgc    5580
ataattctct tactgtcatg ccatccgtaa gatgcttttc tgtgactggt gagtactcaa    5640
ccaagtcatt ctgagaatag tgtatgcggc gaccgagttg ctcttgcccg gcgtcaatac    5700
gggataatac cgcgccacat agcagaactt taaaagtgct catcattgga aaacgttctt    5760
cggggcgaaa aaccagccag ccggaagggc cgagcgcaga gtggtcctg caactttatc    5820
cgcctccatc cagtctatta attgttgccg ggaagctaga gtaagtagtt cgccagttaa    5880
```

-continued

```
tagtttgcgc aacgttgttg ccattgctgc tggcatcgtg gtgtcacgct cgtcgtttgg    5940
tatggcttca ttcagctccg gttcccaacg atcaaggcga gttacatgat cccccatgtt    6000
gtgcaaaaaa gcggttagct ccttcggtcc tccgatcgtt gtcagaagta agttggccgc    6060
agtgttatca ctcatggtta tggcagcact gcataattct cttactgtca tgccatccgt    6120
aagatgcttt tctgtgactg gtgagta                                         6147
```

<210> SEQ ID NO 2
<211> LENGTH: 17
<212> TYPE: DNA
<213> ORGANISM: Artificial sequence
<220> FEATURE:
<223> OTHER INFORMATION: Description of the artificial sequence: Primer M13 forward

<400> SEQUENCE: 2

```
tgaccggcag caaaatg                                                     17
```

<210> SEQ ID NO 3
<211> LENGTH: 19
<212> TYPE: DNA
<213> ORGANISM: Artificial sequence
<220> FEATURE:
<223> OTHER INFORMATION: Description of the artificial sequence: Primer M13 reverse

<400> SEQUENCE: 3

```
ggaaacagct atgaccatg                                                   19
```

<210> SEQ ID NO 4
<211> LENGTH: 26
<212> TYPE: DNA
<213> ORGANISM: Artificial sequence
<220> FEATURE:
<223> OTHER INFORMATION: Description of the artificial sequence: Primer SalEagSF63

<400> SEQUENCE: 4

```
gtcgaccggc cgactcagtc aatcgg                                           26
```

<210> SEQ ID NO 5
<211> LENGTH: 32
<212> TYPE: DNA
<213> ORGANISM: Artificial sequence
<220> FEATURE:
<223> OTHER INFORMATION: Description of the artificial sequence: Primer U3EcoRI

<400> SEQUENCE: 5

```
atcgaattca caacccctca ctcggcgcgc ca                                    32
```

<210> SEQ ID NO 6
<211> LENGTH: 32
<212> TYPE: DNA
<213> ORGANISM: Artificial sequence
<220> FEATURE:
<223> OTHER INFORMATION: Description of the artificial sequence: Primer U3NheI

<400> SEQUENCE: 6

```
atcgctagcg gtggggtctt tcattccccc ct                                    32
```

<210> SEQ ID NO 7
<211> LENGTH: 28
<212> TYPE: DNA

-continued

```
<213> ORGANISM: Artificial sequence
<220> FEATURE:
<223> OTHER INFORMATION: Description of the artificial sequence: Primer
      XhoEagSF65

<400> SEQUENCE: 7
ctcgagcggc cgctagctgc agtaacgc                                              28
```